United States Patent
Lacey et al.

(10) Patent No.: US 9,289,601 B2
(45) Date of Patent: Mar. 22, 2016

(54) SYSTEMS AND METHODS FOR MAKING AND USING A TOOL FOR STEERING A PADDLE LEAD OF AN ELECTRICAL STIMULATION SYSTEM

(71) Applicant: BOSTON SCIENTIFIC NEUROMODULATION CORPORATION, Valencia, CA (US)

(72) Inventors: Natalie Lacey, San Luis Obispo, CA (US); Joshua Dale Howard, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 192 days.

(21) Appl. No.: 14/098,994

(22) Filed: Dec. 6, 2013

(65) Prior Publication Data
US 2014/0171961 A1 Jun. 19, 2014

Related U.S. Application Data

(60) Provisional application No. 61/738,624, filed on Dec. 18, 2012.

(51) Int. Cl.
*A61B 19/00* (2006.01)
*A61N 1/05* (2006.01)

(52) U.S. Cl.
CPC .............. *A61N 1/0553* (2013.01); *A61N 1/05* (2013.01); *A61N 1/0558* (2013.01)

(58) Field of Classification Search
CPC ......... A61N 1/04; A61N 1/05; A61N 1/0551; A61N 1/0553; A61N 1/0558; A61N 2001/0578
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |

(Continued)

FOREIGN PATENT DOCUMENTS

WO 2010114998 A1 10/2010

OTHER PUBLICATIONS

International Search Report and Written Opinion for PCT/US2013/073560 mailed Mar. 4, 2014.

*Primary Examiner* — Melanie Tyson
(74) *Attorney, Agent, or Firm* — Lowe Graham Jones PLLC; Bruce E. Black

(57) ABSTRACT

A paddle lead insertion kit includes a paddle lead and an insertion kit. The paddle lead includes a stylet lumen defined in a paddle body. The insertion tool includes a stylet channel defined along the insertion tool. A stylet is disposed in the stylet channel and transitions between a refracted position and an extended position. When the stylet is in the retracted position, the stylet is disposed completely within the stylet channel. When the stylet is in the extended position, the stylet extends outwardly from the stylet channel and is insertable into the stylet lumen of the paddle lead. A slide assembly is coupled to the stylet and controls transitioning of the stylet between the retracted position and the extended position.

20 Claims, 10 Drawing Sheets

(56) References Cited

U.S. PATENT DOCUMENTS

| | | |
|---|---|---|
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2007/0150036 A1 | 6/2007 | Anderson |
| 2011/0319907 A1* | 12/2011 | Gallegos .............. A61N 1/0541 606/129 |
| 2011/0319909 A1* | 12/2011 | Thenuwara ........ A61B 17/3468 606/129 |
| 2012/0209285 A1 | 8/2012 | Barker et al. |
| 2012/0271315 A1 | 10/2012 | Pianca et al. |

\* cited by examiner

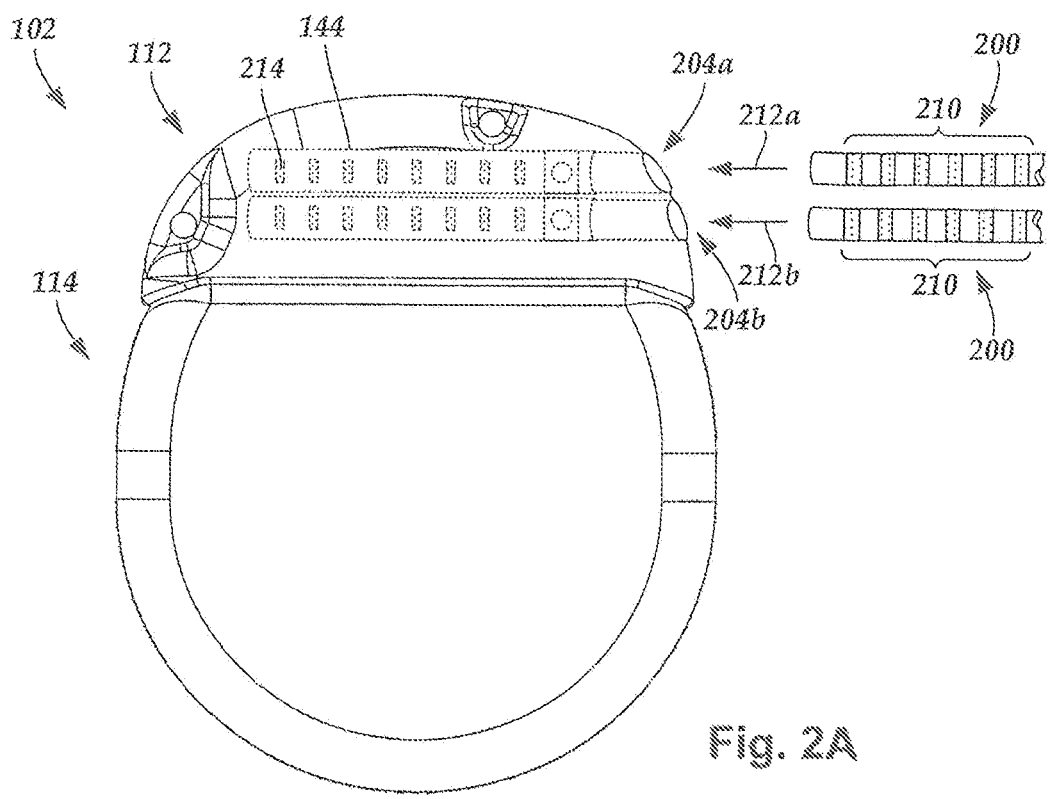

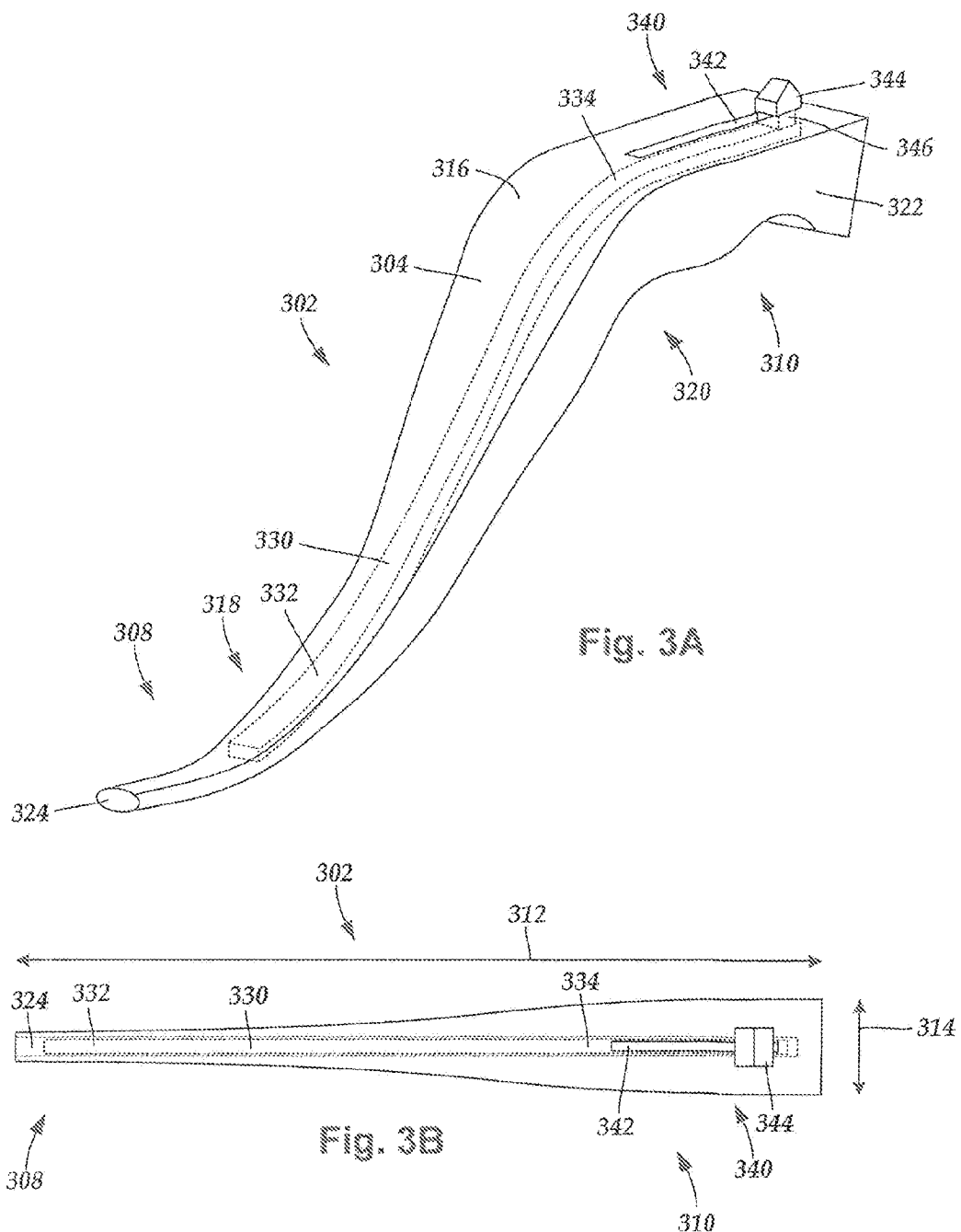

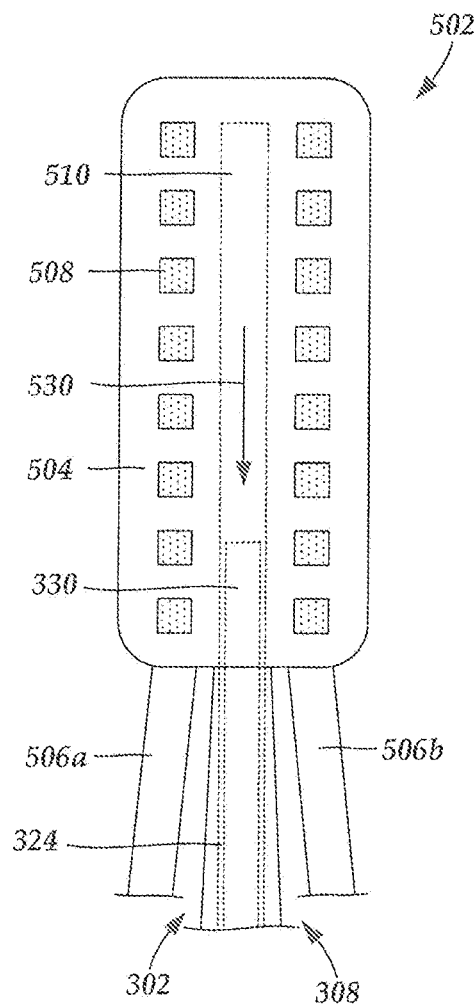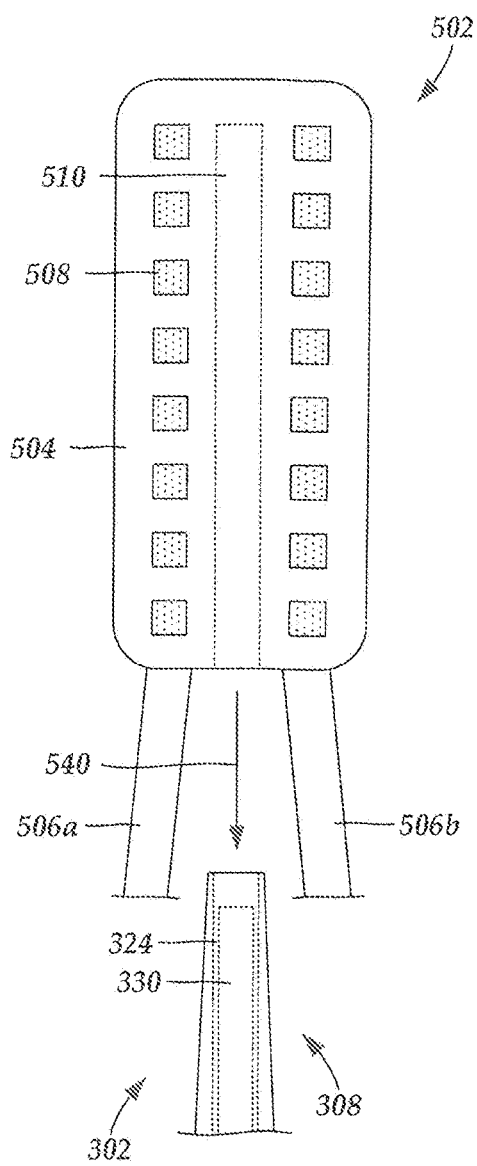

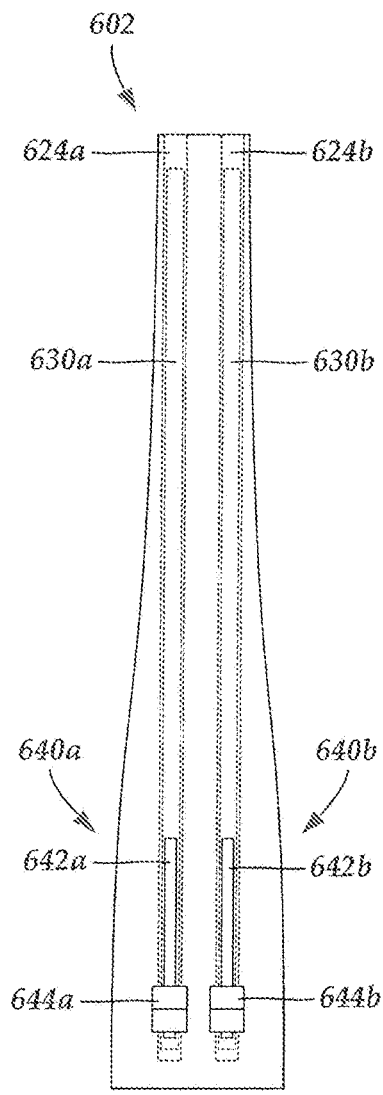
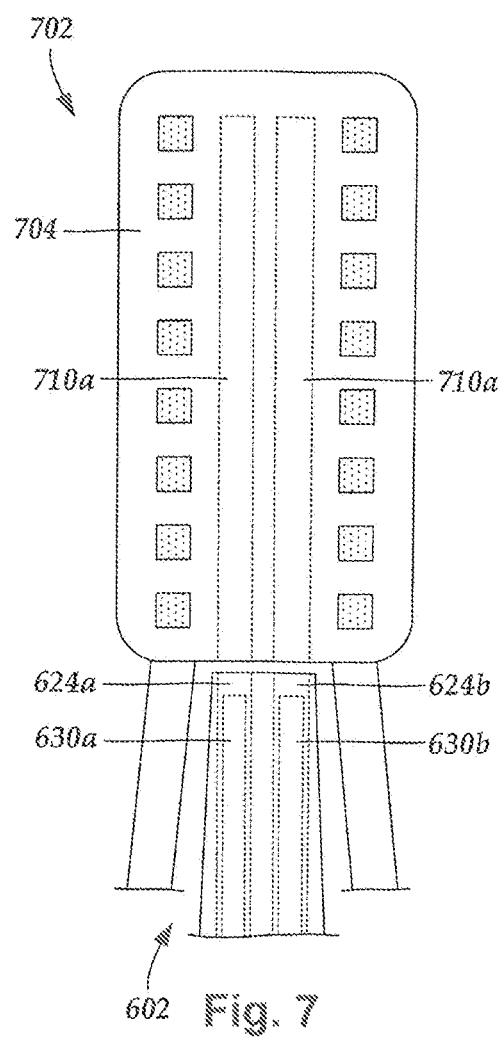

SYSTEMS AND METHODS FOR MAKING AND USING A TOOL FOR STEERING A PADDLE LEAD OF AN ELECTRICAL STIMULATION SYSTEM

CROSS-REFERENCE TO RELATED APPLICATIONS

This application claims the benefit under 35 U.S.C. §119 (e) of U.S. Provisional Patent Application Ser. No. 61/738,624 filed Dec. 18, 2012, which is incorporated herein by reference.

FIELD

The present invention is directed to the area of implantable electrical stimulation systems and methods of making and using the systems. The present invention is also directed to an insertion tool suitable for facilitating implantation of paddle bodies of electrical stimulation leads, as well as methods of making and using the insertion tool, paddle bodies, leads, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a paddle lead insertion kit includes a paddle lead and an insertion kit. The paddle lead includes a paddle body; at least one stylet lumen defined in the paddle body; and at least one lead body having a distal end portion and a proximal end portion. The distal end portion of each of the at least one lead body is coupled to the paddle body. The paddle lead further includes a plurality of electrodes disposed along the paddle body; a plurality of terminals is disposed along the proximal end portion of each of the at least one lead body; and plurality of conductors, where each conductor of the plurality of conductors electrically couples each of the plurality of terminals to at least one of the plurality of electrodes. The insertion tool is configured and arranged for facilitating insertion of the paddle lead into a patient. The insertion tool includes an insertion tool body including an insertion end portion, a handling end portion, an outer surface, and a longitudinal length. A stylet channel extends along the longitudinal length of the insertion tool body from the insertion end portion to the handling end portion. A stylet is at least partially disposed in the stylet channel and is configured and arranged for transitioning between a retracted position and an extended position. The stylet has a first end portion and an opposing second end portion. When the stylet is in the retracted position the first end portion of the stylet is disposed completely within the stylet channel. When the stylet is in the extended position the first end portion of the stylet extends outwardly from the first end portion of the stylet channel and is configured and arranged for insertion into at least one of the at least one stylet lumen of the paddle lead. A slide assembly is disposed along the handling end portion of the insertion tool body and is coupled to the stylet. The slide assembly is configured and arranged to control transitioning of the stylet between the retracted position and the extended position.

In another embodiment, an insertion tool for facilitating insertion of a paddle lead into a patient includes an insertion tool body having an insertion end portion, a handling end portion, an outer surface, and a longitudinal length. The insertion end portion is configured and arranged for insertion into a patient. An insertion tool handle is disposed along the handling end portion of the insertion tool body. The insertion tool handle is configured and arranged for being held in a hand of a user of the insertion tool. A stylet channel extends along the longitudinal length of the insertion tool body from the insertion end portion to the handling end portion. A first end portion of the stylet channel opens along the insertion end portion of the insertion tool body. A stylet is at least partially disposed in the stylet channel. The stylet is configured and arranged for transitioning between a retracted position and an extended position. The stylet has a first end portion and an opposing second end portion. When the stylet is in the retracted position the first end portion of the stylet is disposed completely within the stylet channel. When the stylet is in the extended position the first end portion of the stylet extends outwardly from the first end of the stylet channel and is configured and arranged for insertion into a stylet lumen of a paddle lead. A slide assembly is disposed along the handling end portion of the insertion tool body. The slide assembly is configured and arranged to control transitioning of the stylet between the retracted position and the extended position. The slide assembly includes an actuator slit, an actuator handle, and an actuator strut. The actuator slit is defined along the outer surface of the insertion tool body and extends along at least a portion of the longitudinal length of the insertion tool body. The actuator handle is disposed external to the insertion tool body and over the actuator slit. The actuator handle is configured and arranged for moving along the actuator slit. The actuator strut extends through the actuator slit and couples the actuator handle to the second end portion of the stylet. Movement of the actuator handle along the actuator slit causes a corresponding movement of the stylet along the stylet channel.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2A is a schematic side view of one embodiment of the control module of FIG. 1 configured and arranged to electrically couple to an elongated device, according to the invention;

FIG. 3A is a schematic perspective view of one embodiment of an insertion tool configured and arranged for guiding a paddle lead to a target stimulation location within a patient, according to the invention;

FIG. 3B is a schematic top view of one embodiment of the insertion tool of FIG. 3A, according to the invention;

FIG. 5C is a schematic top view of one embodiment of the portion of the paddle lead and the portion of the insertion tool of FIG. 5B, where a stylet of the insertion tool is being retracted from a stylet lumen of a paddle body of the paddle lead, according to the invention;

FIG. 5D is a schematic top view of one embodiment of the portion of the paddle lead and the portion of the insertion tool of FIG. 5C, where a stylet of the insertion tool is retracted from a stylet lumen of a paddle body of the paddle lead, and the insertion tool is being removed from the paddle body, according to the invention;

FIG. 6 is a schematic top view of another embodiment of an insertion tool, the insertion tool including multiple stylet channels and multiple stylets disposed in the multiple stylet channels, and where the multiple stylets are controllable by multiple slide assemblies, according to the invention;

FIG. 7 is a schematic top view of one embodiment of a portion of a paddle lead and a portion of the insertion tool of FIG. 6, where multiple stylet lumens are disposed in a paddle body of the paddle lead, and where multiple stylets of the insertion tool are configured and arranged for insertion into the stylet lumens of the paddle body, according to the invention;

DETAILED DESCRIPTION

The present invention is directed to the area of implantable electrical stimulation systems and methods of making and using the systems. The present invention is also directed to an insertion tool suitable for facilitating implantation of paddle bodies of electrical stimulation leads, as well as methods of making and using the insertion tool, paddle bodies, leads, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated herein by reference.

Figure 1:
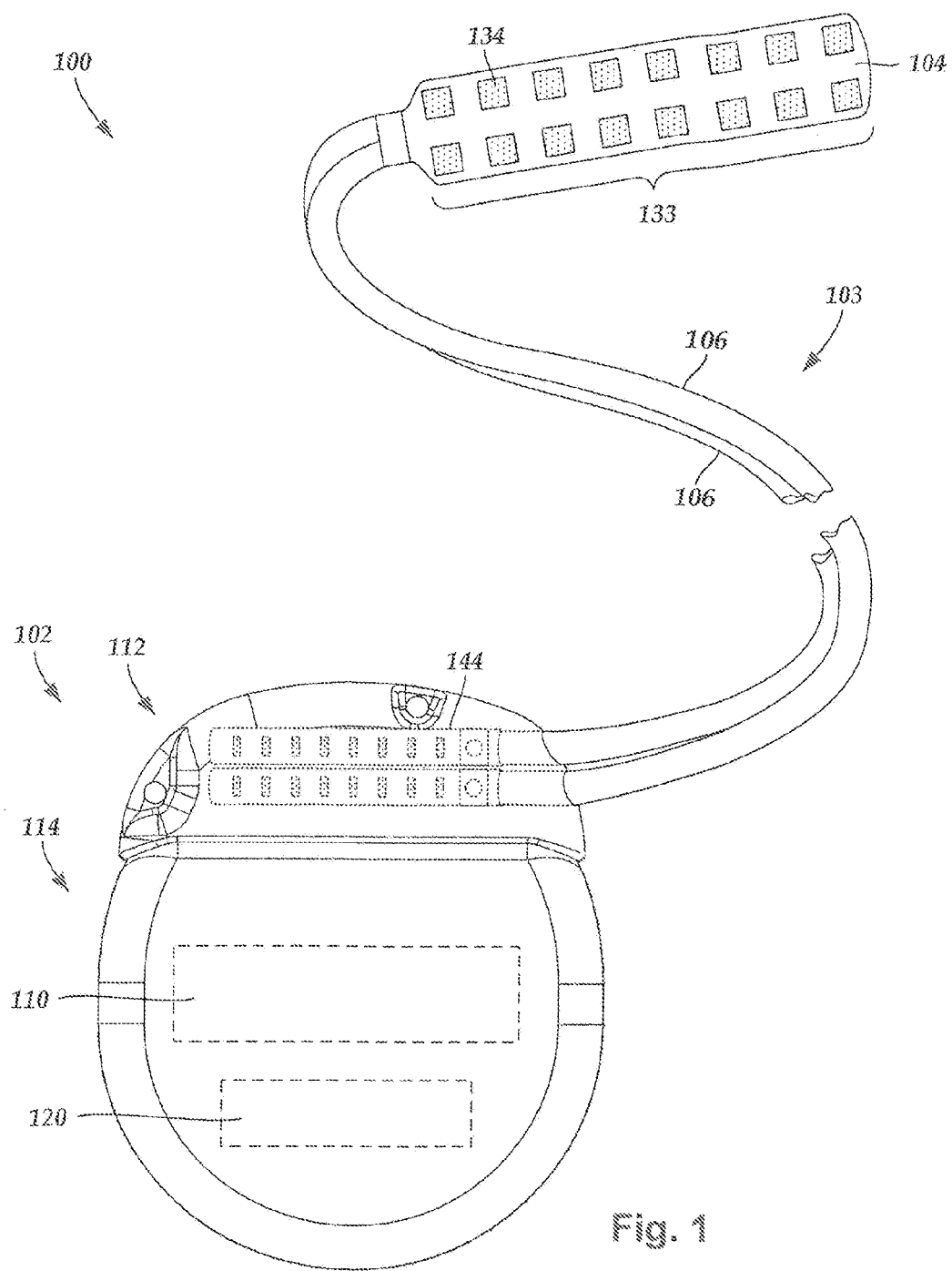
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the paddle body including, for example, four, five, six, seven, eight, nine, ten, eleven, twelve, fourteen, sixteen, twenty-four, thirty-two, or more electrodes 134. The electrodes 134 can be disposed on the paddle body 104 in any suitable arrangement. In FIG. 1, the electrodes 134 are arranged into two columns, where each column has eight electrodes 134.

The electrodes of the paddle body 104 are typically disposed in, or separated by, a non-conductive, biocompatible material such as, for example, silicone, polyurethane, polyetheretherketone ("PEEK"), epoxy, and the like or combinations thereof. The paddle body 104 and the one or more lead bodies 106 may be formed in the desired shape by any process including, for example, molding (including injection molding), casting, and the like. The non-conductive material typically extends from the paddle body 104 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Figure 2B:
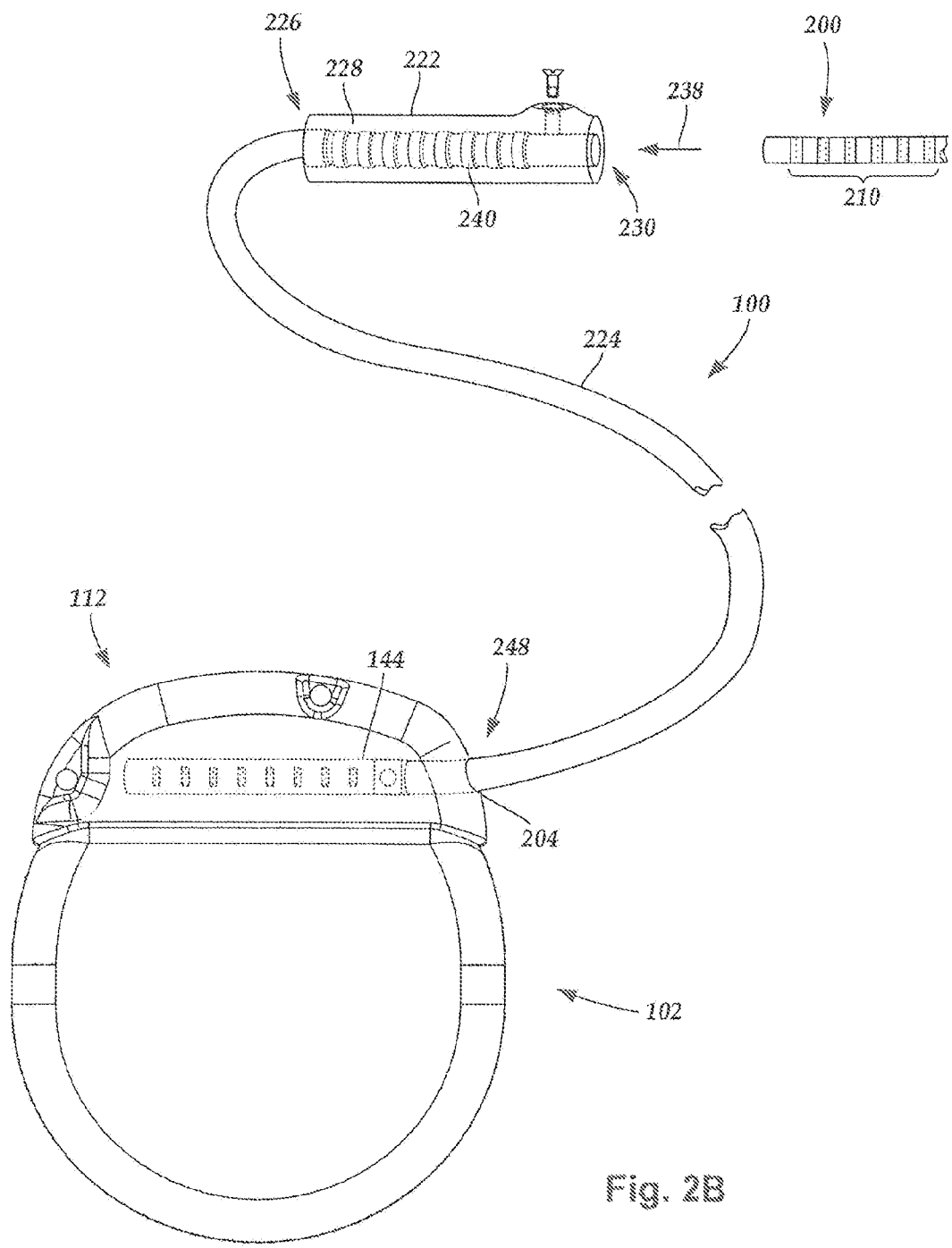
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B). The connector contacts are disposed in connectors (e.g., 144 in FIGS. 1-2B; and 222 FIG. 2B) which, in turn, are disposed on, for example, the control module 102 (or a lead extension, a splitter, an adaptor, or the like). Conductor wires (not shown) extend from the terminals to the electrodes 134. Typically, one or more electrodes 134 are electrically coupled to each terminal. In at least some embodiments, each terminal is only connected to one electrode 134.

The conductor wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, one or more of the lead bodies 106 of FIG. 1, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., one of the lead bodies 106 of FIG. 1, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144 (e.g., the ports 204a and 204b of FIG. 1), or to receive multiple elongated devices 200 (e.g., both of the lead bodies 106 of FIG. 1), or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Turning to FIG. 3A, in at least some embodiments an insertion tool may be used to facilitate advancement of a paddle body to a target stimulation location during implantation of a paddle lead into a patient. Advancing the paddle body to the target stimulation location may involve clearing one or more obstructions and, in the case of spinal cord stimulation, centering the paddle body along the center line of the spinal cord. At least some conventional insertion tools may be difficult to push through patent tissue and to place at a desired location. Additionally, at least some conventional insertion tools may be prone to buckling.

As herein described, insertion tools are described that facilitate insertion of a paddle lead into a patient. The described insertion tools are configured and arranged to couple to the paddle body of the paddle lead. In at least some embodiments, the insertion tools include one or more stylets configured and arranged for insertion into one or more lumens defined in the paddle body.

FIGS. 3A and 3B illustrate an exemplary embodiment of an insertion tool 302 configured and arranged for guiding a paddle lead (see e.g., paddle leads 502 and 702 of FIGS. 5A and 7A, respectively) into a target stimulation location within a patient. The insertion tool 302 includes an insertion tool body 304 having an insertion end portion 308 and a handling end portion 310. The insertion tool body 304 has a longitudinal length 312, a width 314, and an outer surface 316.

Figure 10:
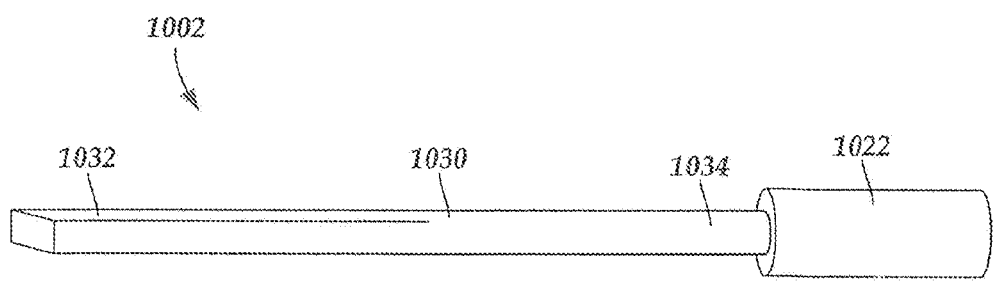
FIG. 10 is a schematic perspective view of another embodiment of an insertion tool, the insertion tool including a handle and a stylet, the stylet having a first end portion and a second end portion, the first end portion having a rectangular cross-section and the second end portion having a round cross-section, according to the invention.

The insertion tool body 304 may have any suitable cross-section including, for example, a rectangular, round, or oval-shaped cross-section. In at least some embodiments, the cross-sectional shape of the insertion tool body 304 may change along the longitudinal length of the insertion tool body 304, as shown in FIG. 10. In at least some embodiments, the width 314 is constant along the longitudinal length 312 of the insertion tool body 304. In at least some other embodiments, the width 314 varies along the longitudinal length 312 of the insertion tool body 304. In at least some embodiments, the handling end portion 310 of the insertion lead body 304 is wider than the insertion end portion 308 of the insertion tool body 304. For example, in at least some embodiments, the width 314 of the insertion tool body 304 tapers. It may be advantageous to design the insertion tool body 304 such that the handling end portion 310 is wider than the insertion end portion 308 because a larger handling end portion 310 may facilitate gripping of the insertion tool 302 by an operator, while a smaller insertion end portion 308 may facilitate insertion of the insertion tool 302 into the patient's body.

The insertion tool body 304 may be formed from multiple post-manufacture pieces that are coupled together by the user. Alternately, the insertion tool body may be manufactured as an integrated structure (e.g., formed as a one-piece structure).

The insertion tool body 304 may include at least one curve along the longitudinal length 312 of the insertion tool body 304. In FIG. 3A, the insertion tool body 304 is shown having a first curve 318 and a second curve 320. It will be understood that insertion tool body 304 may include additional curves. The curve(s) may vary in number, size, or form. In FIG. 3A, the first curve 318 is shown positioned along the insertion end portion 308, while the second curve 320 may be positioned along the handling end portion 310. In at least some embodiment, the first curve 318 and the second curve 320 are oriented oppositely from one another such that the insertion tool body 304 forms an S-shaped configuration along the longitudinal length 312.

It may be advantageous to form the insertion tool body 304 into the S-shaped configuration for facilitating clearance of one or more anatomical structures (e.g., the inferior spinous process) while also allowing for a substantial angular entry into the target stimulation location, for example the epidural space, during insertion of the paddle lead. Moreover, the handling end portion 310 forming one part of the S-shaped configuration may be configured and arranged to enable a user's hand to be held away from an insertion site during an implantation procedure.

Optionally, the handling end portion 310 may include an insertion tool handle 322, dimensioned and sized to fit ergonomically within the hands of a user of the insertion tool 302. The insertion tool handle 322 may include recessed sections to comfortably accommodate a user's fingers and the thumb during applications. In some embodiments, cut outs may be provided on the insertion tool handle 322 for comfortable finger placement. In addition, a cross-sectional profile of the handling end portion 310 may be substantially rectangular with smoothed edges at the corners, making the insertion tool body 304 ergonomic and comfortable to store, hold, and operate. In at least some embodiments, the insertion tool handle 322 is integral with the insertion tool 302. In other embodiments, the insertion tool handle 322 is a separate structure that is configured and arranged for disposing on the insertion tool 302 by the user prior to (or during) use of the insertion tool 302.

In at least some embodiments, the insertion tool 302 defines a stylet channel 324 extending along the longitudinal length 312 of the insertion tool body 304. The stylet channel 324 is configured and arranged to receive one or more stylets 330. The stylet channel 324 may extend from the handling end portion 310 all the way to the insertion end portion 308. The stylet channel 324 may have any suitable cross-sectional profile including, for example, rectangular, round, oval-shaped, cruciform, star-shaped, or the like. In at least some embodiments, the cross-sectional profile of the stylet channel 324 varies along the length of the stylet channel 324.

The stylet 330 includes a first end portion 332 and an opposing second end portion 334. The stylet 330 is disposed within the stylet channel 324 with the first end portion 332 disposed along the insertion end portion 308 of the insertion tool body 304. In at least some embodiments, the stylet 330 is disposed within the stylet channel 324 with the second end portion 334 disposed along the handling end portion 310 of the insertion tool body 304.

Structurally, the stylet 330 may be an elongate, flexible device with enough rigidity to guide a paddle lead. The stylet 330 can be formed from any suitable materials, such as flexible metal wires. In at least some embodiments, the stylet 330 is configured and arranged to remain at least partially disposed within the stylet channel 324. In at least some embodiments, the stylet 330 is configured and arranged to slide along the stylet channel 324 relative to the insertion tool body 304.

The stylet 330 may have any suitable cross-sectional profile including, for example rectangular, round, elliptical, cruciform, star-shaped, or the like. It may be advantageous for the first end portion 332 of the stylet 330 to have a non-round shape to facilitate rotation of the stylet 330 causing a corresponding rotation of the paddle body, when the first end portion 332 of the stylet 330 is inserted into the paddle body. In some embodiments, the stylet 330 is permanently fixed to the insertion tool 302. In other embodiments, the stylet 330 is removable from the insertion tool 302.

In at least some embodiments, the insertion tool 302 includes a slide assembly 340 configured and arranged for controlling movement of the stylet 330 along the stylet channel 324 relative to the insertion tool body 304 along the longitudinal length 312 of the insertion tool body 304. In at least some embodiments, the first end portion 332 of the stylet 330 is configured and arranged to extend outwardly from the stylet channel 324 along the insertion end portion 308 of the insertion tool body 304. In which case, the slide assembly 340 may be configured and arranged for controlling movement of the stylet 330 relative to the insertion tool body 304 (e.g., transitioning of the stylet 330 between retracted and extended positions).

In at least some embodiments, the slide assembly 340 includes an opening or slot defined along the outer surface 316 of the insertion tool body 304, referred to as an actuator slit 342. An actuator handle 344 is disposed over the actuator slit 342 and is configured and arranged to slide along the actuator slit 342. In at least some embodiments, a strut 346 is configured and arranged to couple the actuator handle 344 to the stylet 330 through the actuator slit 342.

In at least some embodiments, the slide assembly 340 is disposed along the handling end portion 310 of the insertion tool 302. In at least some embodiments, the actuator slit 342 extends parallel to the longitudinal length 312 of the insertion tool body 304. In at least some embodiments, the strut 346 is coupled to the second end portion 334 of the stylet 330. In at least some embodiments, the actuator handle 344 is formed as a knob, button, or other tactile feature suitable for moving along the actuator slit 342. In at least some embodiments, the actuator handle 344 is rigidly coupled to the stylet 330 such that movement of the actuator handle 344 along the actuator slit 342 causes a corresponding movement of the stylet 330 along the stylet channel 324.

As mentioned above, the stylet 330 may be configured and arranged for transitioning between a retracted position and an extended position. The slide assembly 340, disposed along the handling end portion 310 and coupled to the stylet 330, may be thus configured and arranged to control such transitioning of the stylet 330 between the retracted position and the extended position.

Therefore, for operations that include the exemplary and aforementioned structural elements of the insertion tool 302, a user of the insertion tool 302 may engage and slide the actuator handle 344 through his or her finger or thumb, to execute motion of the stylet 330 along the stylet channel 324. Such engagement of the actuator handle 344 may optionally be enabled through known manual or automatic mechanisms, or through a combination of such mechanisms.

Figure 4A:
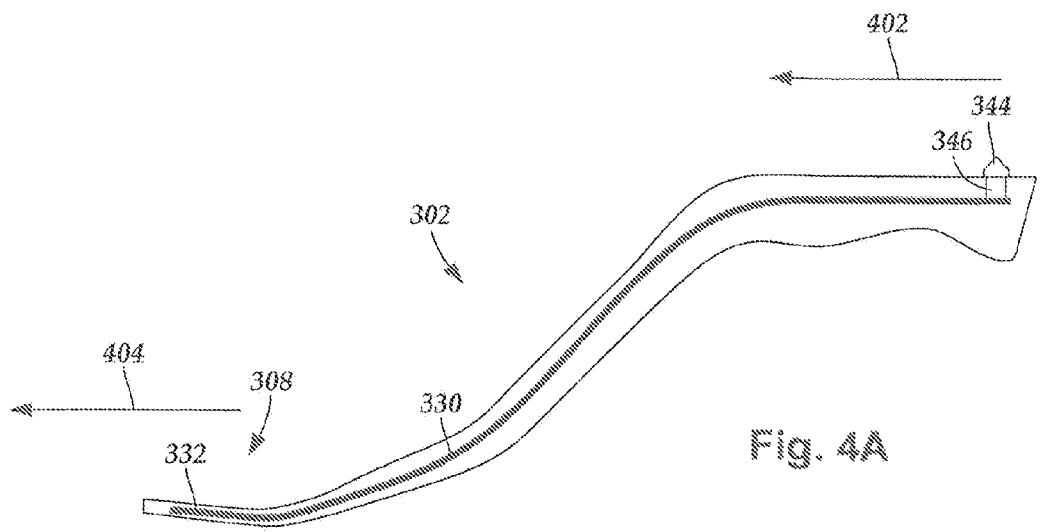
FIG. 4A is a schematic longitudinal cross-sectional view of one embodiment of a stylet disposed in the insertion tool of FIG. 3A, where the stylet is in a retracted position, according to the invention.
Figure 4B:
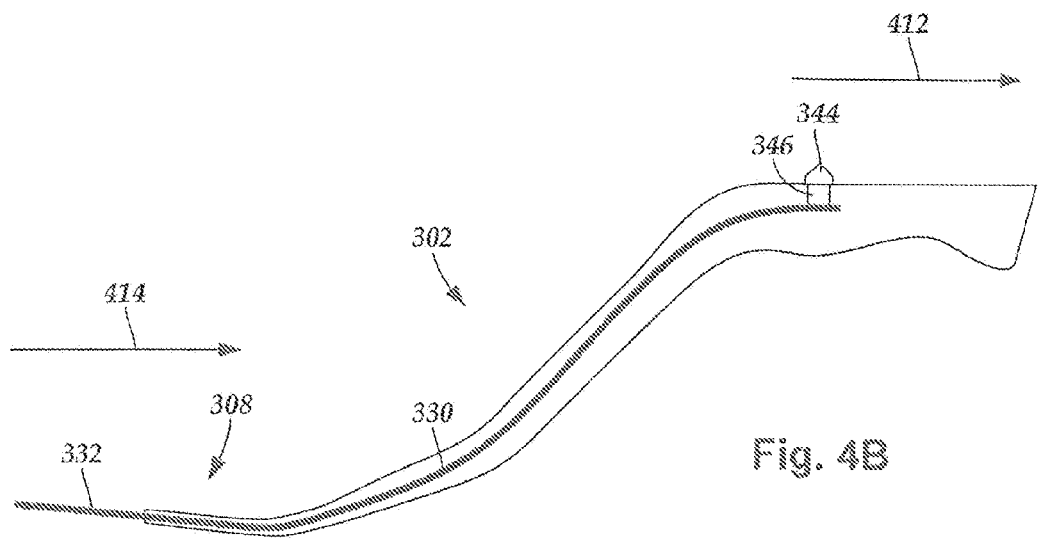
FIG. 4B is a schematic longitudinal cross-sectional view of one embodiment of a stylet disposed in the insertion tool of FIG. 3A, where the stylet is in an extended position with the stylet extending outwardly from an insertion end portion of the insertion tool, according to the invention.

FIGS. 4A-4B show one embodiment of movement of the stylet 330 within the insertion tool 302. FIG. 4A is a side view of one embodiment of the insertion tool 302 with the stylet 330 in a retracted position. FIG. 4B is a side view of the insertion tool 302 with the stylet 330 in an expanded position. In FIG. 4A, the movement of the stylet 330 with respect to the insertion tool 302 from a retracted position to an extended position is shown by arrows 402 and 404. Arrow 402 shows the direction of movement of the actuator handle 344 by a user. Movement of the actuator handle 344 in the direction of the arrow 402 causes a corresponding movement of the strut 346 in the direction of the arrow 402 which, in turn, causes a corresponding movement of the stylet 330 in the direction of the arrow 402. Arrow 404 shows the direction of a corresponding movement of the first end portion 332 of the stylet 330 caused by the movement of the actuator handle 344 in the direction of the arrow 402. As shown in FIG. 4B, when the actuator handle 344 is moved in the direction of the arrow 402, the first end portion 332 of the stylet 330 extends from the insertion end 308 of the insertion tool 302.

In at least some embodiments, extension and retraction limits of the stylet 330 may be realized through the length of the actuator slit 342. In at least some embodiments, the stylet 330 is in a retracted position when the actuator handle 344 is disposed along a lateral portion of the actuator slit 342, as shown in the FIG. 4A. In at least some embodiments, the stylet 330 is in an extended position when the actuator handle 344 is disposed along a medial portion of the actuator slit 342, as shown in the FIG. 4B.

In FIG. 4B, the movement of the stylet 330 with respect to the insertion tool 302 from an extended position to a retracted position is shown by arrows 412 and 414. Arrow 412 shows the direction of movement of the actuator handle 344 by a user. Movement of the actuator handle 344 in the direction of the arrow 412 causes a corresponding movement of the strut 346 in the direction of the arrow 412 which, in turn, causes a corresponding movement of the stylet 330 in the direction of the arrow 412. Arrow 414 shows the direction of corresponding movement of the first end portion 332 of the stylet 330 caused by the movement of the actuator handle 344 in the direction of the arrow 412.

Effectively, the stylet 330 is in the retracted position when the first end portion 332 of the stylet 330 is disposed completely within the stylet channel 324. Conversely, the stylet 330 is in an extended position when the first end portion 332 of the stylet 330 extends outwardly from the stylet channel 324 along the insertion end portion 308 of the insertion tool 302. In at least some embodiments, the stylet channel 324 is coated or lubricated with suitable materials, to allow smooth and precise transition of the stylet 330 relative to the stylet channel 324.

The placement of a medical device, such as a paddle lead, during an implantation procedure may include advancing the paddle lead to the patient's epidural space. During such placement, an accurate functioning of the stylet 330 may be achieved through a substantially flexible stylet 330 that may flex along its length. Accordingly, the stylet 330 may include a substantially flexible elongate body, which may also facilitate its bending at the contours and bends of the stylet channel 324. Bends of the stylet channel 324 occur at the curves 318 and 320, as disclosed above. More particularly, the substantially flexible elongated body of the stylet 330 may allow flexure of the stylet when the stylet 330 is slid back and forth during applications. Therefore, the stylet 330 may be composed of a suitable material, or a combination of suitable materials, that may provide sufficient flexibility to facilitate its bending at different curved portions of the stylet channel 324.

Flexibility of the stylet 330 may be accompanied by structural rigidity as well, preventing the stylet 330 from buckling, or otherwise failing during use. Optionally, the stylet 330 may be configured to include flexibility along a single plane alone, which may restrict flexure and movements of the stylet 330 in other planes. For example, the stylet 330 may include a chained structure, such as those employed in bicycles, which may flex along a single plane, while remaining relatively rigid relative along other planes.

FIGS. 5A-5D show one embodiment of using the insertion tool to implant a paddle lead. FIGS. 5A-5D provide schematic top views of one embodiment of a paddle lead 502, accompanied by a portion of the insertion end portion 308 of the insertion tool 302. The paddle lead 502 includes a paddle body 504, and first and second lead bodies 506*a* and 506*b*, respectively, coupled to the paddle body 504. Electrodes 508 are shown disposed along a major surface of the paddle body 504. The paddle lead 502 may include any suitable number of lead bodies and any suitable number of electrodes 508. A stylet lumen 510 is defined along the paddle body 504. The stylet lumen 510 is configured and arranged to receive the first end portion 332 of the stylet 330.

In FIGS. 5A-5D, the electrodes 508 are shown disposed into two columns, both having equal number of electrodes 508, such that the stylet lumen 510 occupies a space in between the two columns of the electrodes 508. In at least some embodiments, the stylet lumen 510 extends parallel with the columns of electrodes 508. In at least some embodiments, the stylet lumen 510 is disposed between adjacent columns of electrodes 508. In at least some embodiments, the stylet lumen 510 is defined along the paddle body 504 such that an equal number of columns of electrodes 508 are disposed on each side of the stylet lumen 510. Such an arrangement of the stylet lumen 510 within the paddle body 504 may allow the insertion tool 302 to impart a considerably balanced and enhanced maneuvering ability to position the lead effectively during operations.

Figure 5A:
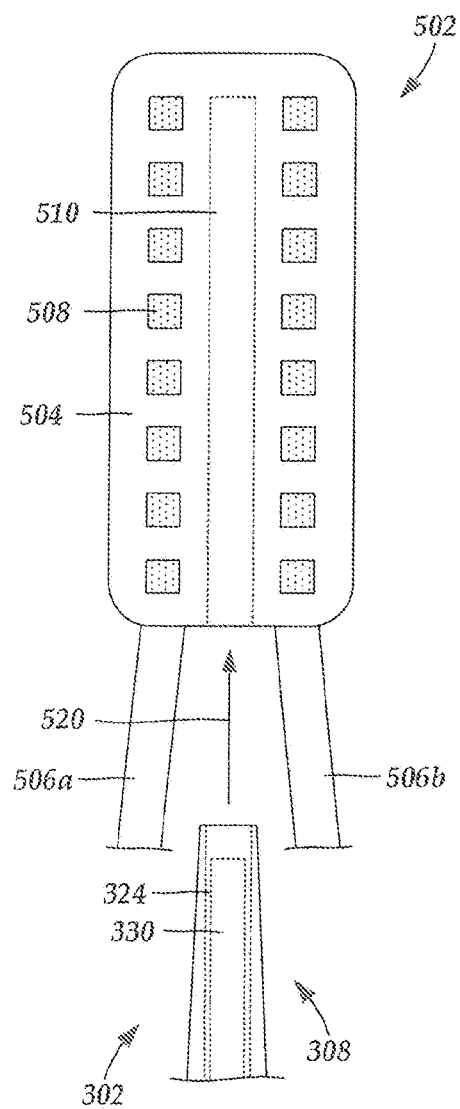
FIG. 5A is a schematic top view of one embodiment of a portion of a paddle lead and a portion of the insertion tool of FIG. 3A, where a stylet lumen is disposed in a paddle body of the paddle lead, and where a stylet of the insertion tool is configured and arranged for insertion into the stylet lumen of the paddle body, according to the invention.

FIG. 5A is a schematic top view of one embodiment of a portion of the insertion tool 302 disposed in proximity to the paddle lead 502. The stylet 330 of the insertion tool 302 is configured and arranged for insertion into the stylet lumen 510. The stylet lumen 510 may include inner boundaries sized and shaped to accommodate the stylet 330. In at least some embodiments, the stylet lumen 510 has a length that is no less than a length of the first end portion 322 of the stylet 330 extended outward from the insertion end portion 308 of the insertion tool 302.

Figure 5B:
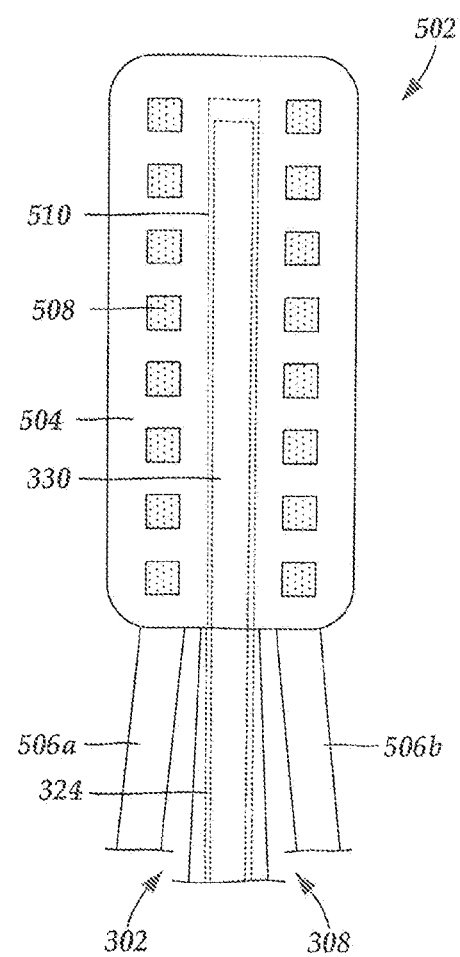
FIG. 5B is a schematic top view of one embodiment of the portion of the paddle lead and the portion of the insertion tool of FIG. 5A, where a stylet of the insertion tool is inserted into a stylet lumen of a paddle body of the paddle lead, according to the invention.

As shown by arrow 520, a user may position the insertion tool 302 outside an opening of the stylet lumen 510 and insert a portion of the stylet 330 of the insertion tool 302 (see FIG. 3A) into the stylet lumen 510 of the paddle body 504. In at least some embodiments, the insertion tool abuts the paddle body 504. FIG. 5B shows the insertion tool 302 abutting the paddle body 504 and the stylet 330 in an extended position with the stylet 330 extended into the stylet lumen 510. In at least some embodiments, a completely inserted first end portion 332 of the stylet 330 can be ensured by the insertion tool 302 abutting the paddle body 504 when the stylet 330 is in the extended position and is inserted into the stylet lumen 510.

Once the stylet 330 is inserted into the paddle lead 502, a user may use the insertion tool 302 to guide, steer, and position, the paddle lead 502 at a target stimulation location within a patient. Once the paddle body 504 of the paddle lead 502 is positioned, the stylet 330 may be removed from the paddle body 504. In at least some embodiments, the stylet 330 is removed from the paddle body 504 without moving the paddle body 504. In which case, removal of the insertion tool 302 can be performed without disrupting the placement of the paddle body 504.

FIG. 5C depicts a schematic top view of a portion of the stylet 330 being retracted from stylet lumen 510 of the paddle lead 502. In FIG. 5C, the stylet 330 is shown being retracted relative to the paddle body 504 in the direction of arrow 530, while the insertion tool 302 remains stationary relative to the paddle body 504. In at least some embodiments, once the stylet 330 is retracted until the first end portion 332 of the stylet 330 is completely disposed in the stylet channel 324, the insertion tool 302 is physically separated from the paddle body 504 and can be removed from the patient, as shown by arrow 540 in FIG. 5D.

Turning to FIG. 6, in at least some embodiments an insertion tool may include multiple stylets. In at least some embodiments, the multiple stylets are controlled independently from one another. FIG. 6 is a schematic top view of one embodiment of an insertion tool 602 that defines a first stylet channel 624*a* and a second stylet channel 624*b*. A first stylet 630*a* is disposed in the first stylet channel 624*a* and a second stylet 630*b* is disposed in the second stylet channel 624*b*.

In at least some embodiments, each of the stylets 630*a* and 630*b* may be controllable by respective slide assemblies. For example, in at least some embodiments, the first stylet 630*a* is controllable via a first slide assembly 640*a* and the second stylet 630*b* is controllable via a second slide assembly 640*b*. The slide assemblies 640 and 640*b* may be configured and arranged to independently control transitioning of their respective stylets 630*a* and 630*b* between retracted positions and extended positions. The slide assemblies 640*a* and 640*b* may include actuator slits 642*a* and 642*b*, respectively. Additionally, in at least some embodiments, the slide assemblies 640*a* and 640*b* may include actuator handles 644*a* and 644*b*, respectively, configured and arranged to couple to the stylets 630*a* and 630*b*, respectively.

FIG. 7 illustrates one embodiments of a paddle lead 702 suitable for being implanted using the insertion tool 602. The paddle lead 702 includes a paddle body 704 that defines a first stylet lumen 710*a* configured and arranged to receive the first stylet 630*a*, and a second stylet lumen 710*b* configured and arranged to receive the second stylet 630*b*. FIG. 7 also depicts a portion of the insertion tool 602 positioned in proximity to the lumens 710*a* and 710*b* and aligned for inserting the stylets 630*a* and 630*b* into the lumens 710*a* and 710*b*, respectively.

A process of insertion of the stylets 630*a* and 630*b* into the pair of stylet lumens 710*a* and 710*b* may be similar to the process described above, with reference to FIG. 5A-5D. Providing multiple, independently-controlled stylets may improve steerability of the paddle lead 702. More specifically, during an insertion and a subsequent application procedure, the actuator handles 644*a* and 644*b* may be operated to slide independent of each other and may thus enable the control of maneuverability variations of the paddle lead 702 in at least one plane. For example, actuator handles 644*a* and 644*b*, controlling the movement of the paddle lead 702 (see FIG. 7), when operating independently, may cause the paddle lead 702 to exemplarily flex and tilt either in the left or the right direction, which may assist in accurately locating the paddle lead at the target stimulation location. Accordingly, such features may enhance paddle lead travel or steering, and may also reduce the travel duration. When operating synchronously, the actuator handles 644*a* and 644*b* may improve stability to the disclosed insertion process.

In other embodiments, a third stylet (not shown) may be arranged that may be operated through a third independently-controlled slide assembly, which may increase control of steering of the paddle lead 702 in another plane. Accordingly, more variations and arrangements may be conceived. Mechanisms and variations to the way in which the paddle lead is steered may be incorporated electronically, automatically, and through other methods.

Figure 8:
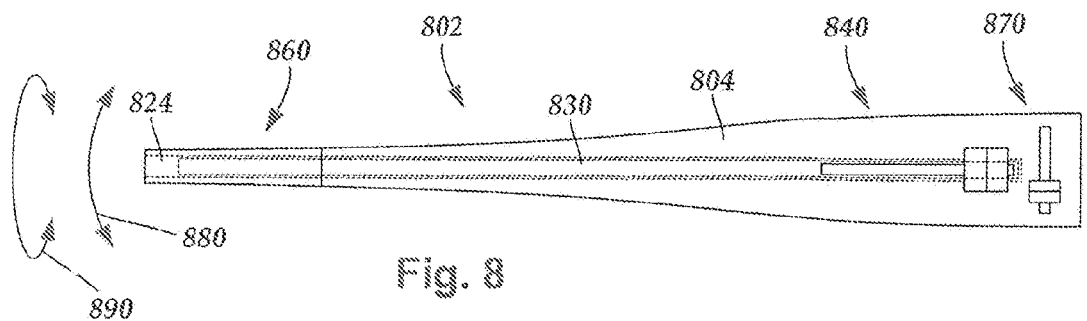
FIG. 8 is a schematic top view of yet another embodiment of an insertion tool, the insertion tool including a distal end portion configured and arranged to rotate independently of the remaining portions of the insertion tool, and a distal movement assembly configured and arranged for controlling bending or rotating of an end portion of the insertion tool relative to other portions of the insertion tool, according to the invention.

Turning to FIG. 8, in at least some embodiments one or more portions of the insertion tool are configured and arranged to rotate or bend (or both) independently from one or more other portions of the insertion tool. FIG. 8 is a schematic top view of one embodiment of an insertion tool 802 having an insertion tool body 804, a stylet channel 824, a stylet 830, and a slide assembly 840. The insertion tool 802 additionally includes a distal end portion 860 and a distal movement assembly 870 configured and arranged to control rotation, or bending, or both, of the distal (i.e., insertion) end portion 860 relative to the remaining portions of the insertion tool body 804.

In at least some embodiments, an interface between the distal end portion 860 and the remaining portions of the insertion tool 802 may include pleated structures, which may allow the distal end portion 860 to move at least along four degrees of freedom with respect to the insertion tool 802. Specifically, such a flexibility may allow the distal end portion 860 to bend in one or more directions relative to the remaining portions of the insertion tool body 804 (arrow 880).

In at least some embodiments, the distal end portion 860 may rotate (arrow 890) in relation to the remaining portions of the insertion tool 802. In this manner, the distal end portion 860 may effectively move along six degrees of freedom. The ability of the distal end portion 860 to rotate, or bend, or both may be constrained angularly, to avoid stylet breakage, which may result from a related torsional force encountered during rotation. Certain conceivable configurations may include the insertion tool 302 to remain fixed, while the distal end portion 860 executes both, a motion along a plane, for example along the plane swept by arrow 880, while rotating about its longitudinal axis simultaneously. Mechanisms and methods to accomplish such features may include well known devices, and may thus be enabled manually, electronically, or automatically.

In application, the rotatable distal end portion 860 may enable the stylet 830 of the insertion tool 802 to angularly enter a stylet lumen of a paddle lead, such as the stylet lumens 510 and 710, discussed above. An angular insertion and a corresponding operation may thus be established. Moreover, such a configuration may specifically enable an operator to steer and locate a corresponding paddle lead at hard to reach places, such as those encountered within an epidural space.

Figure 9:
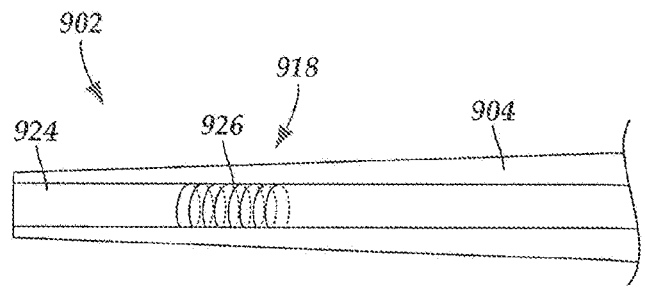
FIG. 9 is a schematic longitudinal cross-sectional view of one embodiment of a portion of an insertion tool, the insertion tool defining a stylet channel formed from a tube having a spiral cut portion, the spiral cut portion of the tube facilitating bending of the insertion tube along the spiral cut, according to the invention.

Turning to FIG. 9, in some embodiments the stylet channel, such as the stylet channel 324, 624a, 624b, or 824, may include provisions to bend or twist, or both, within the insertion tool. FIG. 9 shows one embodiment of an insertion tool 902 that includes an insertion tool body 904 that defines a stylet channel 924. In at least some embodiments, the stylet channel 924 is formed as a tube with a bendable portion 918 configured to adjustably bend (or twist). In at least some embodiments, the stylet channel 924 is formed from metal, such as annealed stainless steel. Optionally, the stylet channel 924 may include an over molded layer of silicone, structured around the stylet channel 924. The malleability of the stylet channel 924, made, for example, from stainless steel, may allow for a substantial amount of flexibility during operations, while the layer of silicone over mold may provide a requisite amount of rigidity to the structure of the stylet channel 924.

In at least some embodiments, the bendable portion 918 of the stylet channel 924 is formed as a spiral cut 926 in the walls of the tube. The spiral cut 926 may be formed through laser cutting and may facilitate bending of the stylet channel 924 along one or more planes. The stylet channel 924 may alternatively include variations in shape and design and may be formed through known methods, all of which may be apparent to those skilled in the art. Additionally, the stylet channel 924 may be made of one or more other materials, such as high-grade plastics, or the like.

Turning to FIG. 10, in at least some embodiments an insertion tool includes a handle having an integrated stylet that is not disposed in a stylet channel. Such an arrangement may be formed, for example, by inserting a stylet, along with its handle, into a related mold during related manufacturing processes, permanently fixing the stylet with the handle. FIG. 10 illustrates a schematic perspective view of another embodiment of an insertion tool 1002. The insertion tool 1002 includes a handle 1022 and a stylet 1030. The stylet 1030 includes a first end portion 1032 and a second end portion 1034 coupled to the handle 1022.

In at least some embodiments, the first end portion 1032 of the stylet 1030 has a cross-sectional profile that is different from a cross-sectional profile of the second end portion 1034. For example, the first end portion 1032 may have a rectangular cross-section while the second end portion 1034 may have a rounded cross-section. The rectangular cross section of the first end portion 1032 may include a tapered flat end, which may ensure a more stable arrangement of the stylet 1030 within a corresponding lumen, whereas the rounded second end portion 1034, which includes the handle 1022, may form an ergonomic grip for an operator.

The handle 1022 may have any suitable cross-sectional shape including for example, triangular, rectangular, rounded, or the like. In at least some embodiments, the handle 1022 includes one or more cutouts for promoting comfortable finger placements for a user of the insertion tool 1002. The insertion tool 1002 may be formed from a moldable material, such as silicone. In at least some embodiments, one or more metal rods (e.g., annealed stainless steel, or the like) are imbedded in the insertion tool 1002 to allow for some changes to the angle at the tapered flat end. In at least some embodiments, the handle 1022 and the stylet 1030 are coupled to one another using threads that are disposed along a portion of the handle 1022 and that mate with threads disposed along a portion of the rounded end of the stylet 1030 disposed at the second end portion 1034.

Figure 11:
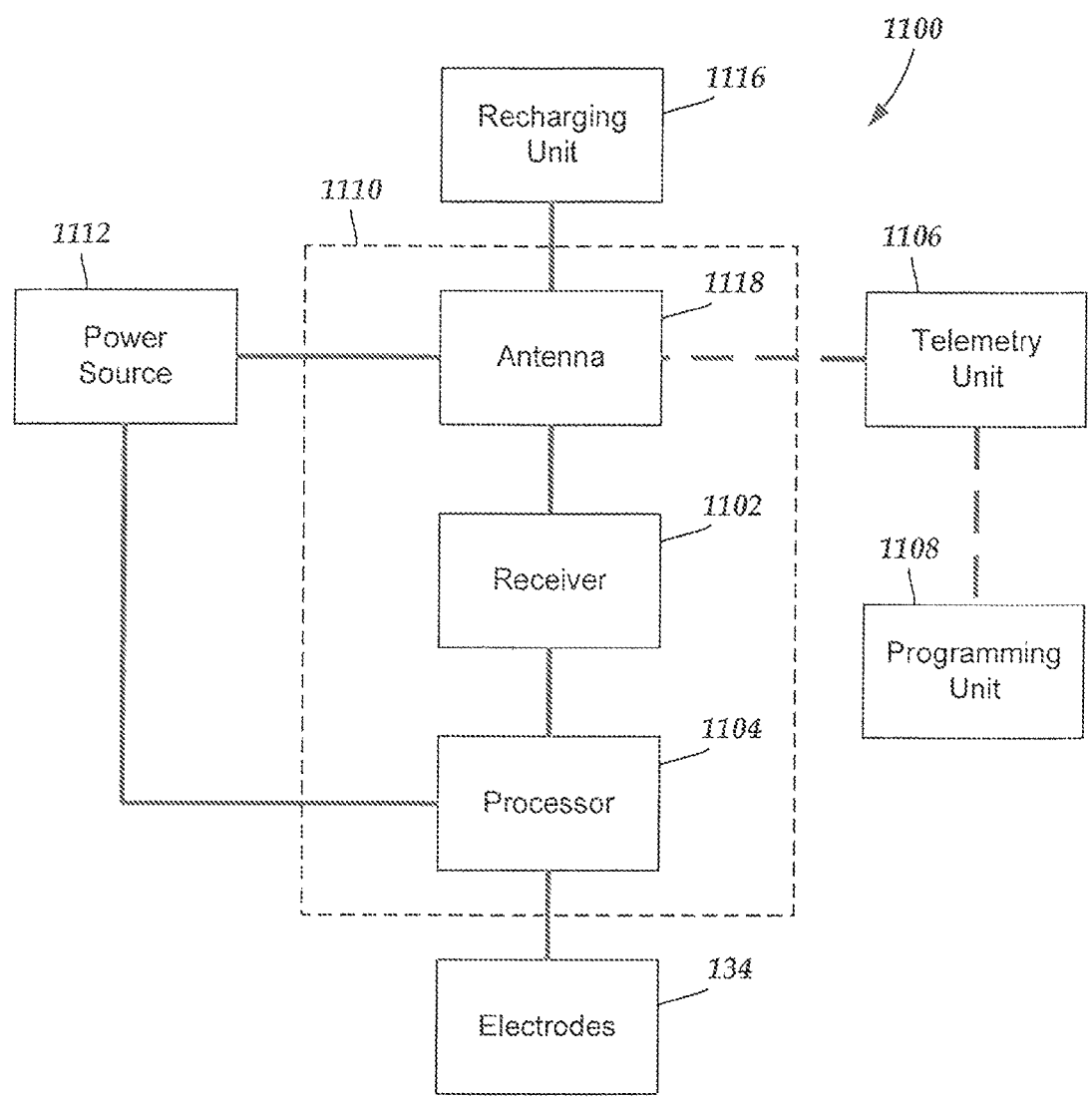
FIG. 11 is a schematic overview of one embodiment of components of a stimulation system, including an electronic subassembly disposed within a control module, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A paddle lead insertion kit, the paddle lead insertion kit comprising:
    a paddle lead comprising
        a paddle body having a proximal end,
        at least one stylet lumen defined in the paddle body with each stylet lumen having an entrance at the proximal end of the paddle body,
        at least two lead bodies, each lead body having a distal end portion and a proximal end portion, wherein the distal end portion of each of the at least two lead bodies is coupled to the paddle body, wherein the entrance of at least one of the at least one stylet lumen is disposed between two of the at least two lead bodies,
        a plurality of electrodes disposed on the paddle body,
        a plurality of terminals disposed along the proximal end portion of each of the at least two lead bodies, and
        a plurality of conductors, each conductor of the plurality of conductors electrically coupling each of the plurality of terminals to at least one of the plurality of electrodes; and
    an insertion tool configured and arranged for facilitating insertion of the paddle lead into a patient, the insertion tool comprising
        an insertion tool body comprising an insertion end portion, a handling end portion, an outer surface, and a longitudinal length,
        a stylet channel extending along the longitudinal length of the insertion tool body from the insertion end portion to the handling end portion,
        a stylet at least partially disposed in the stylet channel, the stylet configured and arranged for transitioning between a retracted position and an extended position, the stylet having a first end portion and an opposing second end portion, wherein when the stylet is in the retracted position the first end portion of the stylet is disposed completely within the stylet channel, wherein when the stylet is in the extended position the first end portion of the stylet extends outwardly from a first end of the stylet channel and is configured and arranged for insertion into at least one of the at least one stylet lumen of the paddle lead, and
        a slide assembly disposed along the handling end portion of the insertion tool body and coupled to the stylet, the slide assembly configured and arranged to control transitioning of the stylet between the retracted position and the extended position.

2. The paddle lead insertion kit of claim 1, further comprising an insertion tool handle disposed along the handling end portion of the insertion tool body, the insertion tool handle configured and arranged for being held in a hand of a user of the insertion tool.

3. The paddle lead insertion kit of claim 1, wherein the stylet has a rectangular cross-section.

4. The paddle lead insertion kit of claim 1, wherein the first end portion of the stylet has a rectangular cross-section and the second end portion of the stylet has a round cross-section.

5. The paddle lead insertion kit of claim 1, wherein the stylet channel has an oval-shaped cross-section.

6. The paddle lead insertion kit of claim 1, wherein the stylet channel comprises a metal tube.

7. The paddle lead insertion kit of claim 6, wherein the metal tube is laser cut in a spiral configuration to facilitate bending of the metal tube.

8. The paddle lead insertion kit of claim 1, wherein the handling end portion of the insertion tool body has a cross-section that is larger than a cross-section of the insertion tool body at the insertion end portion.

9. The paddle lead insertion kit of claim 1, wherein the insertion tool body comprises at least one curve along the longitudinal length of the insertion tool body.

10. The paddle lead insertion kit of claim 1, wherein the insertion tool body comprises at least two curves, the at least two curves oppositely oriented from one another to form an S-shape along the longitudinal length of the insertion tool body.

11. The paddle lead insertion kit of claim 1, wherein the insertion tool body is configured and arranged for bending by a user of the insertion tool prior to insertion of the first end portion of the stylet into the paddle body.

12. The paddle lead insertion kit of claim 1, wherein the slide assembly comprises
    an actuator slit defined along the outer surface of the insertion tool body and extending along at least a portion of the longitudinal length of the insertion tool body;
    an actuator handle disposed external to the insertion tool body and over the actuator slit, the actuator handle configured and arranged for moving along the actuator slit; and
    an actuator strut extending through the actuator slit and coupling the actuator handle to the second end portion of the stylet;
    wherein movement of the actuator handle along the actuator slit causes a corresponding movement of the stylet along the stylet channel.

13. The paddle lead insertion kit of claim 1, wherein the insertion end portion of the insertion tool is configured and arranged to rotate independently from the handling end portion.

14. The paddle lead insertion kit of claim 13, wherein the insertion tool further comprises a rotational actuator configured and arranged for controlling the independent rotation of the handling end portion of the insertion tool.

15. The paddle lead insertion kit of claim 1, wherein the stylet is a first stylet and the stylet channel is a first stylet channel, and wherein the insertion tool further comprises a second stylet that is disposed in a second stylet channel defined in the insertion tool body.

16. The paddle lead insertion kit of claim 15, wherein the slide assembly is a first slide assembly, and wherein the insertion tool further comprises a second slide assembly configured and arranged to control transitioning of the second stylet between the retracted position and the extended position independently from the first stylet.

17. An electrical stimulating system comprising:
    the paddle lead insertion kit of claim 1;
    a control module coupleable to the paddle lead of the paddle lead insertion kit, the control module comprising
        a housing, and
        an electronic subassembly disposed in the housing; and
    a connector for receiving the paddle lead, the connector having a proximal end, a distal end, and a longitudinal length, the connector comprising
        a connector housing defining at least one port at the distal end of the connector, the at least one port configured and arranged for receiving the proximal end of at least one of the at least two lead bodies of the paddle lead, and
        a plurality of connector contacts disposed in the connector housing, the plurality of connector contacts configured and arranged to couple to at least one of the plurality of terminals disposed on the proximal end of at least one of the at least two lead bodies of the paddle lead.

18. A method of inserting an electrical stimulation lead into a patient, the method comprising:
    providing the paddle lead insertion kit of claim 1;
    inserting the first end portion of the stylet of the insertion tool of the paddle lead insertion kit into the stylet lumen defined in the paddle body of the paddle lead of the paddle lead insertion kit;
    using the insertion tool to guide the paddle lead to a target stimulation location;
    retracting the stylet to remove the stylet from the stylet lumen of the paddle body; and
    removing the stylet from the patient.

19. The method of claim 18, wherein retracting the stylet to remove the stylet from the stylet lumen comprises removing the stylet from the stylet lumen of the paddle body without causing corresponding movement of the paddle lead within the patient.

20. The paddle lead insertion kit of claim 1, wherein the paddle body has a lateral width and each of the at least two lead bodies has a lateral diameter, wherein the lateral width of the paddle body is greater than a combination of the lateral diameters of at least two of the at least two lead bodies.

* * * * *